United States Patent [19]

Porret et al.

[11] 3,994,858

[45] Nov. 30, 1976

[54] DIALKOXYPHOSPHONOALKYL DERIVATIVES OF CYCLICUREIDES CONTAINING GLYCIDYL GROUPS

[75] Inventors: Daniel Porret, Binningen; Jürgen Habermeier, Pfeffingen, both of Switzerland

[73] Assignee: Ciba-Geigy Corporation, Ardsley, N.Y.

[22] Filed: Sept. 17, 1975

[21] Appl. No.: 614,038

Related U.S. Application Data

[62] Division of Ser. No. 423,363, Dec. 7, 1973, Pat. No. 3,920,685.

[30] Foreign Application Priority Data

Dec. 12, 1972 Switzerland.................... 18031/72

[52] U.S. Cl. ................. 260/45.8 NZ; 260/45.8 NE; 260/45.8 R

[51] Int. Cl.$^2$........................ C08K 5/35; C08K 5/53
[58] Field of Search.............. 260/45.8 NE, 45.8 NZ

[56] References Cited

UNITED STATES PATENTS

| | | | |
|---|---|---|---|
| 3,890,275 | 6/1975 | Golborn et al..................... | 260/45.8 |
| 3,892,765 | 7/1975 | Porret et al...................... | 260/309.5 |
| 3,925,406 | 12/1975 | Porret et al...................... | 260/309.5 |
| 3,946,034 | 3/1976 | Porret et al...................... | 260/309.5 |

*Primary Examiner*—Lewis T. Jacobs
*Assistant Examiner*—R. A. White
*Attorney, Agent, or Firm*—Vincent J. Cavalieri

[57] ABSTRACT

1-Glycidyl-3-dialkoxyphosphonoalkyl-hydantoins and 1-glycidyl-3-dialkoxyphosphonoalkyl-dihydrouracils. These compounds are used as flame-retardant additives in plastics, especially as additives to epoxide resins.

7 Claims, No Drawings

DIALKOXYPHOSPHONOALKYL DERIVATIVES OF CYCLICUREIDES CONTAINING GLYCIDYL GROUPS

This is a division of application Ser. No. 423,363 filed on Dec. 7, 1973, now U.S. Pat. No. 3,920,685.

The invention relates to 1-glycidyl-3-dialkoxyphosphonoalkyl-hydantoins and 1-glycidyl-3-dialkoxyphosphonoalkyl dihydrouracils, a process for their manufacture and their use as flame-retardant additives in plastics, especially as additives to epoxide resins.

Flame-retardant agents containing phosphorus are already known. To achieve a favourable effect, considerable quantities of these agents, in most cases more than 10%, must be added to the plastics to be protected, but this frequently has an unfavourable effect in other respects, for example mechanical respects, on the protected plastics. It has now been found that the compounds containing phosphorus, according to the invention, render plastics non-inflammable if they are added to the plastics in such amounts that the phosphorus content is at least 0.8 – 4%.

The compounds containing phosphorus, according to the invention, are reactive because of their glycidyl group and after being added to the epoxide resin/curing agent mixtures are built into the polymeric lattice during curing, so that even when used in larger amounts they do not impair the good properties of the cured plastics.

The compounds can above all be employed with advantage in the electrical and electronics field.

The compounds correspond to the formula I

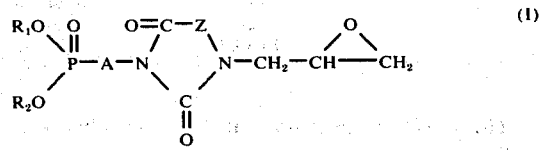

in which Z denotes a nitrogen-free divalent radical which is required to complete a five-membered or six-membered ring, A denotes an alkylene group with 1 – 12 carbon atoms which is optionally interrupted by oxygen atoms and $R_1$ and $R_2$ each denote an alkyl or alkenyl group which can be substituted, for example by halogen, or together denote an alkylene group with 2 to 5 carbon atoms.

Z preferably represents a methyl group which can be substituted by alkyl groups with 1 to 6 carbon atoms, or a cycloalkyl group, such as the methylene group or especially the propylidene-(2,2) group, and also the n- or iso-propylmethylene group, the cyclohexylidene group or cyclopentylidene group, or an ethylene group which is optionally substituted by alkyl groups of 1 to 4 carbon atoms, such as the ethylene, 1,2-dimethylethylene, 2,2-dimethylethylene or 1-methyl-2-isopropylethylene group.

A preferably denotes an alkyl group with 2 to 6 carbon atoms, especially the ethylene group, or the radical of a diethyl ether.

$R_1$ and $R_2$ preferably each denote an alkyl or alkenyl group with 1 to 4 carbon atoms, especially the methyl or ethyl group, but also the propyl, butyl, allyl, butenyl or monochloroethyl group.

The new compounds are manufactured according to known processes by glycidylation of the corresponding 3-dialkylphosphonomethyl-hydantoins or 3-dialkylphosphonomethyl dihydrouracils. The procedure followed is that in a compound of the formula II

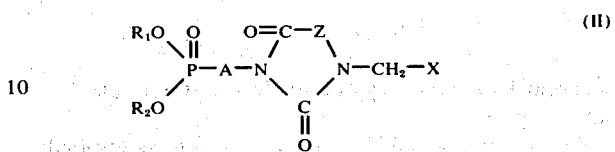

in which X denotes a radical which can be converted into the 1,2-epoxyethyl group, this radical is converted into the epoxyethyl group.

A radical X which can be converted into the 1,2-epoxyethyl radical is above all a hydroxy-halogenoethyl radical which carries the functional groups on different carbon atoms, especially a 2-halogeno-1-hydroxyethyl radical. Halogen atoms are here especially chlorine atoms or bromine atoms. The reaction takes place in the customary manner, above all in the presence of agents which split off hydrogen halide, such as strong alkalis, for example anhydrous sodium hydroxide or aqueous sodium hydroxide solutions. However, it is also possible to use other strongly alkaline reagents, such as potassium hydroxide, barium hydroxide, calcium hydroxide, sodium carbonate or potassium carbonate.

A further radical X which can be converted into the 1,2-epoxyethyl radical is, for example, the ethenyl radical, which can be converted into the 1,2-epoxyethyl radical in a known manner by means of per-compounds, such as, above all, by reaction with hydrogen peroxide or per-acids, for example peracetic acid, perbenzoic acid or monoperphthalic acid.

The starting substances of the formula II are obtained in a manner which is in itself known. Thus it is possible to react a compound of the formula III

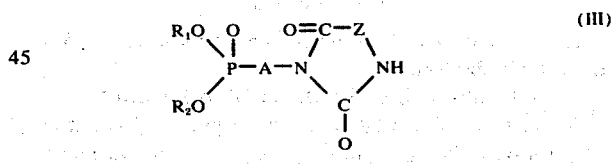

under mild conditions with a compound of the formula X-CH$_2$-Hal, wherein Hal represents a halogen atom and X has the abovementioned meaning. Preferably, the compound of the formula III is reacted with an epihalogenohydrin, above all epihalogenohydrin, in the presence of a catalyst, such as, in particular, a tertiary amine, a quaternary ammonium base or a quaternary ammonium hydroxide.

The compounds of the formula III can be obtained by reacting a compound of the formula IV

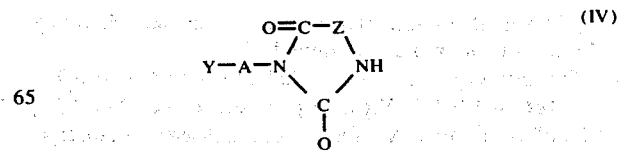

wherein Y denotes chlorine or bromine, with a trialkyl-phosphite of the formula V

wherein $R_3$ denotes an optionally substituted alkyl or alkenyl group.

For bringing about the reaction, which corresponds to a Michaelis-Arbusow reaction, the mixture is usually warmed over the course of several hours to above 100° C, preferably 120° – 160° C, in the course of which RY, that is to say, for example, methyl chloride, ethyl chloride, butyl chloride or 1,2-dichloroethane, distils off.

The compounds of the formula IV are obtained by reaction of the corresponding hydantoins or dihydrouracils which are unsubstituted in the 3-position, with a compound of the formula VI

wherein Hal denotes chlorine or bromine, in the presence of agents which split off hydrogen halide, such as alkalis or strongly basic salts, for example sodium carbonate. Examples of compounds of the formula VI are $\beta,\beta'$-dichloroethane or $\beta,\beta'$-dichlorodiethyl ether.

The products according to the invention are liquid to viscous substances which are colourless in the pure state. They can be purified by vacuum distillation.

The new substances are very suitable for use as additives to customary epoxide resins to render them non-inflammable or flame-retardant. For this purpose they have the advantage of a low viscosity in most cases, so that they simultaneously exert a certain action as a reactive diluent.

The parts in the examples which follow denote parts by weight.

EXAMPLES 1. 1-Glycidyl-3-(dimethoxyphosphonoethyl)-5,5-dimethylhydantoin a. 3-($\beta$-Chloroethyl)-5,5-dimethyl-hydantoin A mixture of 1,664 g of 5,5-dimethyl-hydantoin (13.0 mols), 897 g of anhydrous potassium carbonate (6.5 mols), 5,148 g of 1,2-dichloroethane (52 mols) and 1,458 ml of dimethylformamide is reacted for 18 hours and 20 minutes at 90° C to 100° C internal temperature (external temperature 155° C), whilst constantly removing the resulting water of reaction by azeotropic circulatory distillation. Water of reaction eliminated: 110 g (94.0% of theory). Thereafter the reaction mixture, whilst still hot, is separated by filtration from the potassium chloride produced, the filtrate concentrated on a rotary evaporator at 100° C and the residue is dried to constant weight at 100° C and $10^{-1}$ mm Hg.

2,385 g of a clear brown, highly viscous substance (96.2% of theory) are obtained.

The crude product is distilled at 0.1 to 0.2 mm Hg and 146° – 149° C: Yield of pure substance, 2,068.3 g (83.4% of theory). A sample recrystallised from methanol melts at 95.8° to 96.2° C and has the following analytical data:

| Found: | Calculated: |
|---|---|
| 44.13% C | 44.10% C |
| 5.91% H | 5.82% H |
| 14.67% N | 14.70% N |
| 18.54% Cl | 18.60% Cl | b. 3-(Dimethoxyphosphonoethyl)-5,5-dimethylhydantoin

A mixture of 381.3 g of 3-(2'-chloroethyl)-5,5-dimethyl-hydantoin (2.0 mols) and 322.6 g of trimethyl phosphite (2.6 mols) is reacted at 120° C (bath temperature 180° C). The methyl chloride produced in the reaction is condensed in a cold trap at −80° C, for the purpose of following the course of the reaction. After 39 hours the reaction has ended, the internal temperature has at that point risen to 190° C, and 96.7 g of methyl chloride (95.7% of theory) are obtained. The reaction product is freed of readily volatile constituents in a waterpump vacuum at 110° C and is then dried to constant weight at $10^{-1}$ mm Hg and 105° C.

490 g of a yellowish, clear, highly viscous crude product (92.7% of theory) are obtained, showing the following analytical data: 9.80% of phosphorus and 0.2% of chlorine.

A crude product purified by distillation in a bulb tube (at 140° – 160° C external temperature and $10^{-1}$ mm Hg) and subsequent crystallisation from ethyl acetate melts at 101.2° – 102.6° C.

| Elementary analysis: | Found: | Calculated: |
|---|---|---|
| | 40.93% C | 40.91% C |
| | 6.72% H | 6.49% H |
| | 10.54% N | 10.60% N |
| | 11.65% P | 11.72% P |

The H-NMR spectrum can be reconciled with the following structure:

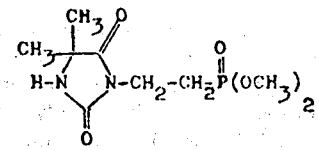

c. 1-Glycidyl-3-(dimethoxyphosphonoethyl)-5,5-dimethyl-hydantoin

A mixture of 132.1 g of 3-(dimethoxyphosphonoethyl)-5,5-dimethyl-hydantoin (0.5 mol), 463 g of epichlorohydrin (5.0 mols) and 0.5 g of tetramethylammonium chloride is stirred for 100 minutes at 118° C. The mixture is then cooled to 60° C; 44 g of 50% strength sodium hydroxide solution (0.55 mol) are added dropwise over the course of 3 hours with vigorous stirring, under a waterpump vacuum; at the same time the water present in the reaction mixture is removed continuously by azeotropic circulatory distillation. To complete the reaction, distillation is continued for a further 30 minutes after the dropwise addition; the mixture is then cooled to 20° C, the sodium chloride which has precipitated is filtered off and the epichlorohydrin solution is concentrated on a rotary evaporator under a waterpump vacuum. The product is then dried to constant weight at 100° C and $10^{-1}$ mm Hg.

143.3 g (89.5% of theory) of a yellow, clear, viscous resin are obtained, of which the epoxide content is 3.07 epoxide equivalents/kg (98.4% of theory). The product contains 0.8% of chlorine and 7.54% of phosphorus (theory 9.67% P).

2. 1-Glycidyl-3-(diethoxyphosphono-n-butyl)-5,5-dimethyl-hydantoin a. 3-(4-Chlorobutyl)-5,5-dimethyl-hydantoin A mixture of 538 g of 5,5-dimethyl-hydantoin (4.2 mols), 290 g of anhydrous potassium carbonate (2.1 mols) and 2,130 g of 1,4-dichlorobutane (16.77 mols) is reacted for 8 hours at 138° to 141° C internal temperature (external temperature 200° C), as described under Example 1 (a). Working up is carried out according to Example 1 (a), and 830.9 g of a brown, viscous crude product (90.5% of theory) are obtained, and are purified by vacuum distillation (boiling point$_{0.2}$: 151°–153° C) and subsequent recrystallisation from diethyl ether. The pure product melts at 54.4° to 56.3° C.

| Analytical data: | Found: | Calculated: |
| --- | --- | --- |
| | 49.26% C | 49.43% C |
| | 7.02% H | 6.91% H |
| | 13.1 % N | 12.81% N |
| | 15.72% Cl | 16.21% Cl | b. 3-(Diethoxyphosphono-n-butyl)-5,5-dimethyl-hydantoin 43.9 g of 3-(4-chloro-n-butyl)-5,5-dimethyl-hydantoin (0.2 mol) and 39.9 g of triethyl phosphite are reacted for 31 hours at 163° to 205° C (bath temperature 184° to 220° C) in the manner described under Example 1 (b), ethyl chloride being split off. The mixture is worked up analogously to Example 1 (b) and 60.1 g of a clear, yellow, viscous substance are obtained (93.9% of theory). Analytical data: 8.95% P, <0.3% chlorine. Distillation in a bulb tube (external temperature: 140° – 160° C and 0.03 mm Hg) gives a clear, colourless, viscous distillate which displays the following analytical data:

| Elementary analysis: | Found: | Calculated: |
| --- | --- | --- |
| | 48.69% C | 48.74% C |
| | 7.74% H | 7.87% H |
| | 8.97% N | 8.75% N |
| | 9.47% P | 9.67% P | c. 1-Glycidyl-3-(diethoxyphosphone-n-butyl)-5,5-dimethyl-hydantoin 48.1 g of 3-(diethoxyphosphone-n-butyl)-5,5-dimethyl-hydantoin (0.15 mol), 139 g of epichlorohydrin (1.5 mols) and 0.15 g of tetramethylammonium chloride are stirred for 90 minutes at 115° – 118° C, in the manner described under Example 1 (c). The solution is then cooled to 60° C and 13.2 g of 50% strength aqueous sodium hydroxide solution are added dropwise over the course of 3 hours. The water is constantly removed by azeotropic circulatory distillation. After a further 30 minutes, the reaction is complete, and the mixture is worked up as described under Example 1 (c). 38.4 g of a clear, yellow, viscous resin (68% of theory) are obtained, having an epoxide content of 2.62 epoxide equivalents/kg (98.8% of theory). A vacuum distillation in a bulb tube (external temperature 156° – 160° C, 0.02 mm Hg) gives a clear, colourless, viscous distillate having an epoxide content of 2.66 epoxide equivalents/kg (98.5% of theory).

| Elementary analysis: | Found: | Calculated: |
| --- | --- | --- |
| | 50.80% C | 51.06% C |
| | 7.74% H | 7.77% H |
| | 7.68% N | 7.44% N |
| | 8.31% P | 8.23% P |

3. 1-Glycidyl-3-(diethoxyphosphonoethyl)-5-ethyl-5-methyl-hydantoin a. 3-(β-Chloroethyl)-5-ethyl-5-methyl-hydantoin 284.3 g of 5-ethyl-5-methyl-hydantoin (2.0 mols), 138.2 g of anhydrous potassium carbonate (1.0 mol), 791.7 g of 1,2-dichloroethane (8.0 mols) and 230 ml of dimethylformamide are subjected to an azeotropic circulatory distillation for 25 hours at 90° C to 107° C internal temperature (external temperature: 160° C), in the manner described under Example 1 (a). After completion of the reaction, the mixture is filtered whilst still hot and the filtrate is concentrated on a rotary evaporator at 90° C under a waterpump vacuum. The reaction mixture is then dried to constant weight at 90° C and 10$^{-1}$ mm Hg. 392.5 g of a brown, clear, product (95.9% of theory) are obtained, and are purified by vacuum distillation (boiling point$_{0.2}$: 147° C). Yield of pure product: 327.3 g (80% of theory). A sample recrystallised from diethyl ether melts at 58.0° C to 59.0° C.

| Analytical data: | Found: | Calculated: |
| --- | --- | --- |
| | 47.23% C | 46.95% C |
| | 6.56% H | 6.40% H |
| | 13.61% N | 13.69% N |
| | 17.36% Cl | 17.32% Cl | b. 3-(Diethoxyphosphonoethyl)-5-ethyl-5-methyl-hydantoin 102.3 g of 3-(2-chloroethyl)-5-ethyl-5-methyl-hydantoin (0.5 mol) and 99.8 g of triethyl phosphite (0.6 mol) are reacted at 161° C to 182° C, analogously to Example 1 (a). The reaction mixture is worked up analogously to Example 1 (a) and 127 g of a light yellow, clear, viscous substance (83% of theory) are obtained. Distillation in a bulb tube (external temperature: 148° C to 160° C; 0.04 mm Hg) gives a colourless, viscous distillate which displays the following analytical data:

| Elementary analysis: | Found: | Calculated: |
| --- | --- | --- |
| | 47.15% C | 47.06% C |
| | 7.79% H | 7.57% H |
| | 9.22% N | 9.15% N |
| | 10.04% P | 10.11% P | c. 1-Glycidyl-3-(diethoxyphosphonoethyl)-5-ethyl-5-methyl-hydantoin 61.2 g of 3-(diethoxyphosphonoethyl)-5-ethyl-5-methyl-hydantoin (0.2 mol), 277.5 g of epichlorohydrin (3.0 mols) and 0.2 g of tetramethylammonium chloride are stirred for 90 minutes at 115° – 119° C. The mixture is then cooled to 60° C and 17.6 g of 50% strength aqueous sodium hydroxide solution are added dropwise over the course of 4 hours whilst stirring, under a waterpump vacuum. The water present in the mixture is removed by azeotropic circulatory distillation analogously to Example 1 (c). The mixture is worked up analogously to Example 1 (c) and 65.7 g of a yellow, clear, viscous resin (90.6% of theory) having an epoxide content of 2.71 epoxide equivalents/kg (96.7% of theory) are obtained. The product contains 0.65% of chlorine and 6.72% of phosphorus.

4. β-(Dimethoxyphosphono)-β'-(1-glycidyl-5,5-dimethyl-hydantoin-3-yl)-diethyl ether a. 3-(3-Oxy-5-chloro-pentyl)-5,5-dimethyl-hydantoin 640 g of 5,5-dimethyl-hydantoin (5.0 mols), 345.5 g of anhydrous potassium carbonate (2.5 mols) and 2,860 g of β,β'-dichlorodiethyl ether (20.0 mols) are subjected to an azeotropic circulatory distillation for 6 hours and 20 minutes at 121° to 152° C internal temperature (external temperature 170° C). The working up takes place analogously to that described under Example 1 (a) and 994 g of a brown, viscous crude product (84.7% of theory) are obtained. Vacuum distillation and subsequent recrystallisation from diethyl ether gives pure β-chloro-β'-(5,5-dimethyl-hydantoinyl-3)-diethyl ether (or 3-(3-oxa-5-chloro-pentyl)-5,5-dimethyl-hydantoin) having a melting point of 55.4° C to 57.4° C.

| Elementary analysis: | Found: | Calculated: |
|---|---|---|
|  | 45.99% C | 46.06% C |
|  | 6.41% H | 6.44% H |
|  | 11.73% N | 11.94% N |
|  | 14.92% Cl | 15.11% Cl | b. β-(Dimethoxyphosphono)-β'-(5,5-dimethyl-hydantoin-3-yl)-diethyl ether 70.4 g of β-chloro-β'-(5,5-dimethyl-hydantoin-3-yl)-diethyl ether (0.3 mol) and 48.4 g of trimethyl phosphite are reacted for 48 hours and 25 minutes at 120° C to 189° C bath temperature. After 48 hours and 25 minutes the reaction is complete and 14.9 g of methyl chloride (98.3% of theory) have been eliminated. The mixture is worked up analogously to Example 1 (b) and 84.3 g of a clear, yellow, viscous product (91.1% of theory) are obtained, displaying the following analytical data: 8.70% of phosphorus and <0.3% of chlorine.

c. β-(Dimethoxyphosphono)-β'-(1-glycidyl-5,5-dimethyl-hydantoin-3-yl)-diethyl ether 67.0 g of β-(dimethoxyphosphono)-β'-(5,5-dimethyl-hydantoin-3-yl)-diethyl ether (0.217 mol), 201 g of epichlorohydrin (2.17 mols) and 0.2 g of tetramethylammonium chloride are stirred for 90 minutes at 116° – 118° C. The mixture is then cooled to 60° C, 19 g of 50% strength aqueous sodium hydroxide solution are added dropwise over the course of 3 hours and 15 minutes, and the water is removed by azeotropic circulatory distillation. The mixture is worked up analogously to Example 1 (c) and 48 g of a yellow, viscous resin (60.7% of theory) are obtained, having an epoxide content of 2.47 epoxide equivalents/kg (90.2% of theory). Phosphorus content: 6.8%.

5. 1-Glycidyl-3-(diethoxyphosphonoethyl)-5,5-dimethyl-hydantoin a. 3-(Diethoxyphosphonoethyl)-5,5-dimethyl-hydantoin 704.1 g of 3-(2-chloroethyl)-5,5-dimethyl-hydantoin (3.0 mols) [manufactured according to Example 1(a)] and 598.5 g of triethyl phosphite are stirred at 162° to 188° C. The elimination of ethyl chloride is complete after 22 hours and 20 minutes and the reaction product is worked up analogously to Example 1 (b). 859.8 g of a yellow, clear, viscous substance (98.0% of theory) are obtained, having a phosphorus content of 8.6%.

b. 1-Glycidyl-3-(diethoxyphosphonoethyl)-5,5-dimethyl-hydantoin

A mixture of 146.1 g of 3-(diethoxyphosphonoethyl)-5,5-dimethyl-hydantoin (0.5 mol), 694 g of epichlorohydrin (7.5 mols) and 0.5 g of tetramethylammonium chloride is stirred for 105 minutes at 105° C. 44 g of 50% strength aqueous sodium hydroxide solution are added dropwise over the course of 3 hours at 60° C, analogously to Example 1 (c). The mixture is worked up analogously to Example 1 (c) and 157 g of a yellow, clear resin (90.2% of theory) with 2.74 epoxide equivalents/kg (95.5% of theory) and a phosphorus content of 6.13% are obtained.

6. 1-Glycidyl-3-(dimethoxyphosphonoethyl)-5,5-pentamethylene-hydantoin a. 3-(β-Chloroethyl)-5,5-pentamethylene-hydantoin 336.4 g of 5,5-pentamethylene-hydantoin (2.0 mols), 138.2 g of anhydrous potassium carbonate (1.0 mol), 791.7 g of 1,2-dichloroethane (8.0 mols) and 300 ml of dimethylformamide are reacted as described under Example 1 (a). After a reaction time of 21¾ hours at 101° C to 117° C internal temperature (external temperature 160° C) the reaction is complete and the reaction mixture is filtered whilst still hot. The filtrate is worked up analogously to Example 1 (a). 460.8 g of a brownish, crystalline product, (99.86% of theory) having a melting point of 154° C to 156.4° C are obtained. Recrystallisation of the crude product from toluene in the ratio of 1:1.6 gives the pure compound, of melting point 156° to 158° C, in 86% yield.

| Found: | Calculated: |
|---|---|
| 51.83% C | 52.06% C |
| 6.67% H | 6.55% H |
| 12.27% N | 12.14% N |
| 15.11% Cl | 15.37% Cl |

The 60 Mc H-NMR spectrum is consistent with the following structure:

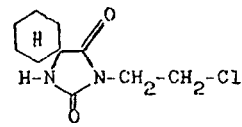

b. 3-(Dimethoxyphosphonoethyl)-5,5-pentamethylene-hydantoin 48.4 g of trimethyl phosphite (0.39 mol) are added dropwise over the course of 115 minutes to 69.3 g of 3-(β-chloroethyl)-5,5-pentamethylene-hydantoin (0.3 mol) at 165° – 170° C. After 20 hours and 45 minutes, the elimination of methyl chloride has ceased. The reaction mixture is worked up as described in Example 1 (b) and 84.3 g of a solid, yellow product (92.3% of theory) containing 8.9% of phosphorus and <0.3% of chlorine are obtained.

c. 1-Glycidyl-3-(dimethoxyphosphonoethyl)-5,5-pentamethylene-hydantoin 60.8 g of 3-(dimethoxyphosphonoethyl)-5,5-pentamethylene-hydantoin (0.2 mol), 277.5 g of epichlorohydrin (3.0 mols) and 0.2 g of tetramethylammonium chloride are stirred for 90 minutes at 116° – 120° C. Thereafter, the mixture is cooled to 60° C and 17.6 g of 50% strength aqueous sodium hydroxide solution are added dropwise over the course of 3 hours, analogously to Example 1 (c). The mixture is worked up analogously to Example 1 (c) and 54.3 g of a brown, clear, viscous resin (75% of theory) having an epoxide content of 1.84 epoxide equivalents/kg are obtained.

Use Examples

I.

A mixture, containing 2.41% of phosphorus, of 120 parts of the product manufactured according to Example 1, 143 parts of hexahydrophthalic anhydride and 143 parts of an industrially manufactured triglycidyl compound from 1,3-bis-(5',5'-dimethyl-hydantoin-3-yl)-propan-2-ol, containing 6.1 epoxide equivalents/kg, is converted to a clear, homogeneous liquid at 100° C and poured into a prewarmed aluminium mould.

Curing takes place in 2 hours/120° C + 16 hours/150° C. Mouldings having the following properties are obtained:

| | |
|---|---|
| Inflammability: (CTM20*) | Level ½ inch |
| Heat distortion point according to Martens (DIN): | 103° C |
| Impact strength (VSM 77,105) | 11.0–14.0 cm kg/cm² |
| Flexural strength (VSM 77,103) | 10.5–15.8 kg/mm² |
| Deflection | 4.6 mm |
| Water absorption (4 days, 20° C) | 1.55% |

*CTM 20: Description of the test: A horizontally clamped DIN standard bar (120×50×10 mm) of the plastic which is to be tested is exposed for 1 minute to the flame of a Bunsen burner which is inclined at 45° and fed with town gas (burner orifice: 9 mm, flame height with burner vertical: 10 cm), so that the 15 mm wide surface of the test specimen is 3 cm above the upper edge of the burner and the end face is at a horizontal distance of 1 cm from the lower edge of the burner.

What we claim is:

1. A flame-retardant composition comprising an epoxide resin and a compound of the formula

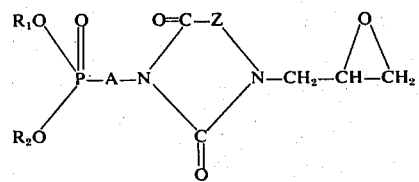

wherein Z is methylene, methylene substituted with alkyl groups of 1 to 6 carbon atoms, cyclohexylidene, or cyclopentylidene; A is alkylene of 1 to 12 carbon atoms, or $-CH_2CH_2OCH_2CH_2-$; $R_1$ and $R_2$ each is alkyl or alkenyl of 1 to 4 carbon atoms, or $R_1$ and $R_2$ together is alkylene of 2 to 5 carbon atoms, wherein said compound is present in the composition in such an amount that the phosphorus content is at least 0.8 to 4%.

2. The flame-retardant composition according to claim 1 wherein Z is propylidene-(2,2).

3. The flame-retardant composition according to claim 1 wherein $R_1$ and $R_2$ each is alkyl or alkenyl of 1 to 4 carbon atoms.

4. The flame-retardant composition according to claim 1 wherein $R_1$ and $R_2$ is each ethyl or methyl.

5. The flame-retardant composition according to claim 1 wherein A is alkylene of 2 to 6 carbon atoms.

6. The flame-retardant composition according to claim 1 wherein A is ethylene.

7. The flame-retardant composition according to claim 1 wherein A is $-CH_2CH_2OCH_2CH_2-$.

* * * * *